US010537659B2

(12) United States Patent
Alexander et al.

(10) Patent No.: US 10,537,659 B2
(45) Date of Patent: Jan. 21, 2020

(54) 3D PRINTED POLYVINYL ALCOHOL MEDICAL DEVICES AND METHODS OF ACTIVATION

(71) Applicant: Board of Supervisors of Louisiana State University and Agricultural and Mechanical College, Baton Rouge, LA (US)

(72) Inventors: Jonathan Steven Alexander, Shreveport, LA (US); Christen J. Boyer, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/721,561

(22) Filed: Sep. 29, 2017

(65) Prior Publication Data

US 2019/0099516 A1   Apr. 4, 2019

(51) Int. Cl.

| B29C 71/02 | (2006.01) |
| B29C 71/04 | (2006.01) |
| A61L 27/16 | (2006.01) |
| A61L 31/16 | (2006.01) |
| A61L 31/04 | (2006.01) |
| A61L 31/00 | (2006.01) |

(Continued)

(52) U.S. Cl.
CPC ............. *A61L 27/16* (2013.01); *A61L 27/025* (2013.01); *A61L 27/24* (2013.01); *A61L 27/26* (2013.01); *A61L 27/38* (2013.01); *A61L 27/54* (2013.01); *A61L 27/60* (2013.01); *A61L 31/005* (2013.01); *A61L 31/028* (2013.01); *A61L 31/041* (2013.01); *A61L 31/044* (2013.01); *A61L 31/048* (2013.01); *A61L 31/16* (2013.01); *B29C 64/10* (2017.08); *B29C 64/106* (2017.08); *B29C 64/112* (2017.08); *B29C 64/118* (2017.08); *B29C 64/30* (2017.08); *B33Y 10/00* (2014.12); *B33Y 40/00* (2014.12); *B33Y 70/00* (2014.12); *C08F 116/06* (2013.01); *A61L 2300/404* (2013.01); *A61L 2300/406* (2013.01); *A61L 2300/414* (2013.01); *A61L 2300/416* (2013.01); *A61L 2430/34* (2013.01); *B29C 2035/085* (2013.01); *B29C 2035/0877* (2013.01); *B29K 2029/04* (2013.01); *B29L 2031/753* (2013.01); *B29L 2031/7532* (2013.01); *B29L 2031/7534* (2013.01); *B33Y 80/00* (2014.12); *C08F 2810/20* (2013.01)

(58) Field of Classification Search
CPC ...... B29C 2035/085; B29C 2035/0877; B29C 64/106; B29C 64/112; B29C 64/118; B29C 71/02; B29C 71/04; B29K 2029/04; B29L 2031/753; B29L 2031/7532; B29L 2031/7534; B33Y 10/00; B33Y 70/00; C08F 116/06; C08F 2810/20
USPC .................... 264/236, 308, 331.11, 485, 488
See application file for complete search history.

(56) References Cited

U.S. PATENT DOCUMENTS 4,552,138 A * 11/1985 Hofeditz ............. A61L 26/0014
424/445
6,096,216 A * 8/2000 Shanbrom .............. A01N 59/12
210/198.2

(Continued)

*Primary Examiner* — Leo B Tentoni
(74) *Attorney, Agent, or Firm* — Charles G. Holoubek; Davis & Bujold, PLLC (57) ABSTRACT

A medical device comprising a structure formed of polyvinyl alcohol.

16 Claims, 6 Drawing Sheets
(6 of 6 Drawing Sheet(s) Filed in Color)

(51) Int. Cl.

| | | |
|---|---|---|
| *A61L 27/54* | (2006.01) | |
| *A61L 27/60* | (2006.01) | |
| *A61L 27/38* | (2006.01) | |
| *A61L 31/02* | (2006.01) | |
| *A61L 27/02* | (2006.01) | |
| *A61L 27/24* | (2006.01) | |
| *A61L 27/26* | (2006.01) | |
| *B29C 64/10* | (2017.01) | |
| *B29C 64/30* | (2017.01) | |
| *B33Y 40/00* | (2015.01) | |
| *B33Y 70/00* | (2015.01) | |
| *B33Y 10/00* | (2015.01) | |
| *C08F 116/06* | (2006.01) | |
| *B29C 64/106* | (2017.01) | |
| *B29C 64/112* | (2017.01) | |
| *B29C 64/118* | (2017.01) | |
| *B29L 31/00* | (2006.01) | |
| *B33Y 80/00* | (2015.01) | |
| *B29K 29/00* | (2006.01) | |
| *B29C 35/08* | (2006.01) | |

(56) References Cited

U.S. PATENT DOCUMENTS

2008/0149561 A1\* 6/2008 Chu .................. A61L 15/425
                                                            210/500.38
2018/0071502 A1\* 3/2018 Hakim ................ A61M 29/02

\* cited by examiner

3D PRINTED POLYVINYL ALCOHOL MEDICAL DEVICES AND METHODS OF ACTIVATION

BACKGROUND

Tissue replacements suffer from a lack of appropriate donors, tissue typing, availability, homogeneity and variety leading to the failure in many cases of transplants. In the case of autotransplants for example, mammary artery or femoral vein substitutes for coronary artery bypass, the tissue from which these tissues are taken can lead to stress or injury. Current 3D printing for tissues is a highly complex process and requires a specialized laboratory and printing facility using complex and highly expensive materials. There is a need for a wider variety of tissue types which can be used to take the place of diseased or damaged tissues. Further, currently, polyvinyl alcohol (PVA) is used in 3D printing as a water soluble support matrix which can rapidly dissolve to permit complex structure printing. PVA in its unmodified state though, is challenging to use for biological devices. For the foregoing reasons, there is a pressing, but seemingly irresolvable need for a flexible, biologically compatible scaffolding, able to covalently bind growth factors and act as a support matrix for integrating living cells.

SUMMARY

Wherefore, it is an object of the present invention to overcome the above mentioned shortcomings and drawbacks associated with the current technology.

The present invention is directed to methods and apparatuses that satisfy the above shortcomings and drawbacks.

The disclosed invention is related to methods and medical devices comprising a structure formed of polyvinyl alcohol. According to a further embodiment the polyvinyl alcohol is cross-linked. According to a further embodiment the polyvinyl alcohol is cross-linked by a reaction including an aldehyde. According to a further embodiment the aldehyde is glutaraldehyde. According to a further embodiment a medically functional chemical is loaded onto the structure. According to a further embodiment the medically functional chemical is iodine. According to a further embodiment the medically functional chemical is one of Bromine, a divalent cation, a protein, an antibiotic, and an anti-cancer drug, a therapeutic, a regulatory molecule, a matrix molecule, a guidance molecule, a growth factor, collagen, a stem cell matrix, a smooth muscle cell matrix, and a cell. According to a further embodiment the medically functional chemical is one of Zinc, Copper, and Iron II. According to a further embodiment the medical device is one of a vascular stent, a product for use in a non-vascular anatomical space, a wound care product, a wound dressing, an antimicrobial surface, a vascular access graft, a coronary artery bypass grafts, a skin replacement, a duct replacement, a bone replacement, and a vascular conduit.

The disclosed invention is further related to devices and methods for creating a medical device comprising 3D printing the medical device out of polyvinyl alcohol. According to a further embodiment the polyvinyl alcohol is crosslink with an aldehyde. According to a further embodiment the crosslinking of the polyvinyl alcohol with the aldehyde is facilitated with an acid. According to a further embodiment the acid is HCl. According to a further embodiment the crosslinking of the polyvinyl alcohol with the aldehyde is facilitated by elevating a temperature of the polyvinyl alcohol and the aldehyde to a temperature of between 40 degrees and 200 degrees for a set time. According to a further embodiment the set time is between 6 and 48 hours. According to a further embodiment the crosslinking of the polyvinyl alcohol with the aldehyde is facilitated by exposure to one of gamma and electron beam radiation. According to a further embodiment a medically functional chemical is loaded onto the polyvinyl alcohol. According to a further embodiment the medically functional chemical is one of iodine, one of Bromine, a divalent cation, a protein, an antibiotic, an anti-cancer drug, a therapeutic, a regulatory molecule, a matrix molecule, a guidance molecule, a growth factor, collagen, a stem cell matrix, a smooth muscle cell matrix, and a cell. According to a further embodiment the medically functional chemical is iodine and further comprising a step of loading the iodine on the polyvinyl alcohol via gas sublimation. According to a further embodiment the medical device is formed into one of a vascular stent, a product for use in a non-vascular anatomical space, a wound care product, a wound dressing, an antimicrobial surface, a vascular access graft, a coronary artery bypass grafts, a skin replacement, a duct replacement, a bone replacement, and a vascular conduit.

The present invention relates to methods for generating biologically compatible 3D printing scaffolds which can be printed on demand and which support cell engraftment because of the high level of protein binding which is a result of the stabilization process. These matrices are inert biologically, resorbable and once generated can be stored frozen until needed.

The present invention further relates to using gas and liquid phase polymerization of polyvinyl alcohol using aldehyde and hydrochloric acid treatment to create both rigid and flexible, yet insoluble and biologically compatible scaffolds, suitable for creating synthetic blood vessels, conduits, vascular access grafts and other tissue replacements. The disclosed chemical modification using aldehyde, and optionally hydrochloric acid, converts PVA to a crosslinked form which is preferably 1) flexible, 2) biologically compatible, 3) able to covalently bind growth factors, and other protein or amine containing factors including antibiotics, amino acids and matrix proteins. In some embodiments, the crosslinked PVA can act as a support matrix for integrating living cells.

The disclosed approach stabilizes conventional 3D prints using 'off the shelf' printing methods. Importantly, variations in the processing of polyvinyl alcohol prints can generate both matrices with properties of bone to blood vessels to skin grafts. This approach solves issues with cost, variety of methods used to create graft/replicants and availability that are present and otherwise unresolved with the current technology.

The successful completion of these aims is intended to provide a simple and highly accessible tissue 'printing' approach using simple and inexpensive materials which are rendered biologically stable and compatible by the chemical modification which stabilizes the grafts. The approach to modify the graft after its stabilization allows for the addition of a larger number of molecules including combinations of molecules which may be highly controllable and which can support development of a large number of tissue printing methods. The avoidance of 'hot printing' of temperature sensitive proteins by second step modification achieves a long sought goal of 3D bioprinting, namely the stable incorporation of important regulatory, matrix and guidance molecules without which grafts often fail.

Another object of the present invention is to use patient anatomy to generate custom replicants based on MR or CT imaging.

A further object of the invention is to engraft replicant scaffolds with stem cells to create a limitless variety of tissue types for engraftment.

A still further object of the invention is the ability to covalently modify these replicants with any growth factor or guidance molecule which is a shortcoming of current methodologies.

The invention relates to tissue grafts and methods for creating tissue grafts comprising chemically crosslinking polyvinyl alcohol to a patient; this could represent tissue replacements following breast cancer, kidney cancer, colon cancer, rectal cancer, ovarian cancer, stomach cancer, uterine cancer, carcinoma in situ, etc. as well as vascular prosthesis, bone replacements, tooth replacements, etc). This method permits the elegent chemical modification of the graft to covalently attach growth factors, peptides, matrix molecules and/or cells which are difficult to retain in biological environments. This permits the generation of a long duration environment which can support angiogenesis, tissue repair and integration.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which.

DETAILED DESCRIPTION

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Figures 1A, 1B:
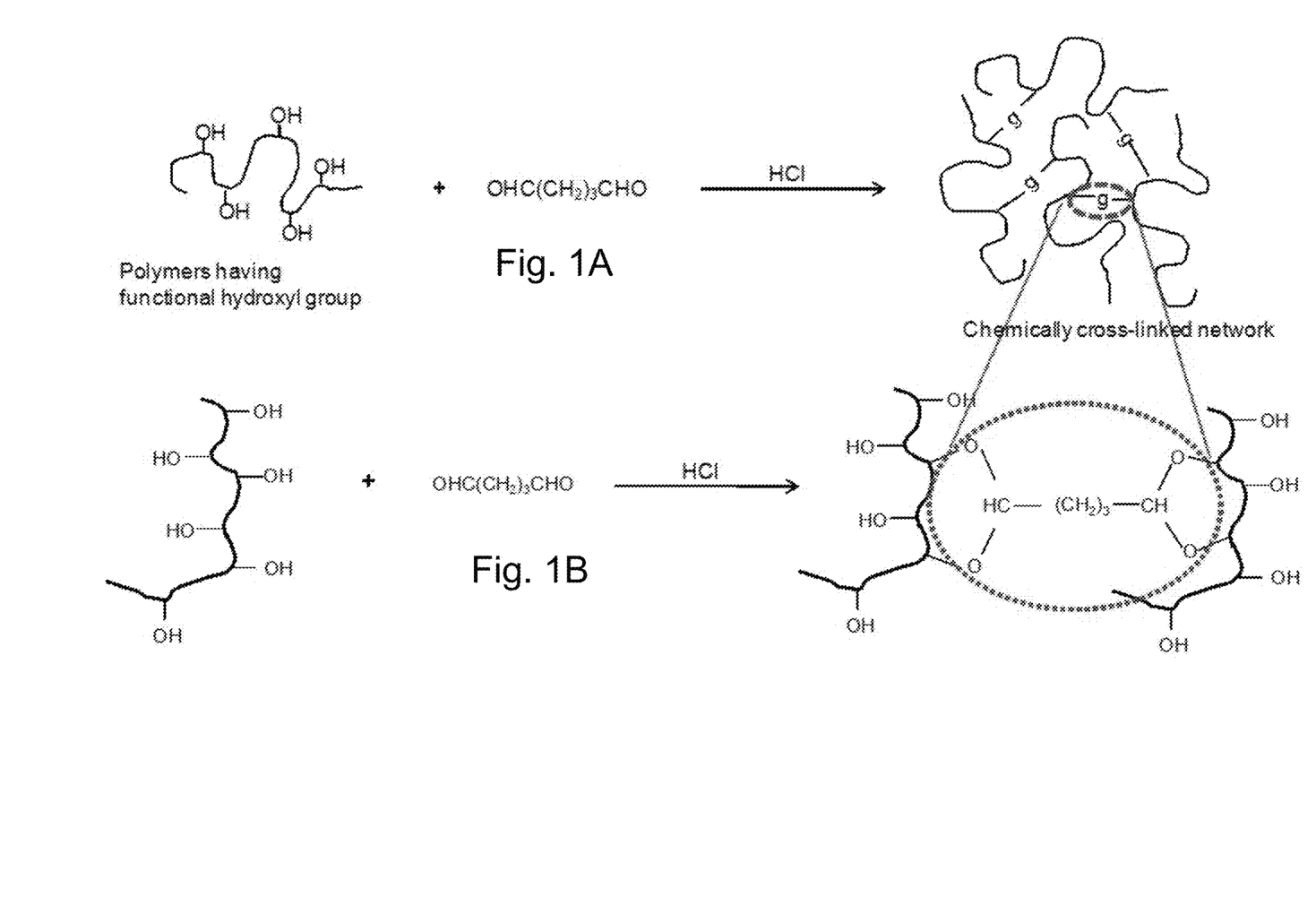
FIG. 1A is a schematic diagram of the chemistry for PVA crosslinking and FIG. 1B is a of a schematic diagram of the chemistry for PVA crosslinking with an enlargement of a portion of FIG. 1A to show more chemical details of the crosslinking.

Turning now to FIGS. 1-6D, a brief description concerning the various components of the present invention will now be briefly discussed. As can be seen in FIG. 1, the crosslinking of the scaffold is likely never 'complete' and an aldehyde side chain will remain which can be used to bind additional modifier proteins or peptides.

Figure 2A:
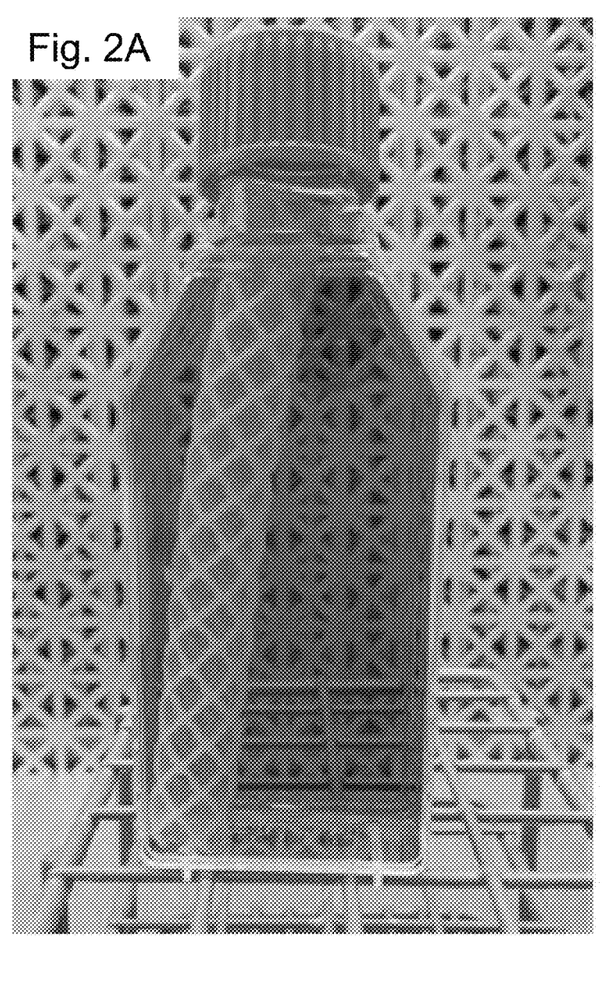
FIGS. 2A and 2B are a photographs of a scaffold prepared by the disclosed method containing stem cells to generate a vascular prosthesis, with FIG. 2A showing the prosthesis in a bottle and FIG. 2B showing a close-up of the prosthesis in FIG. 2A.
Figure 2B:
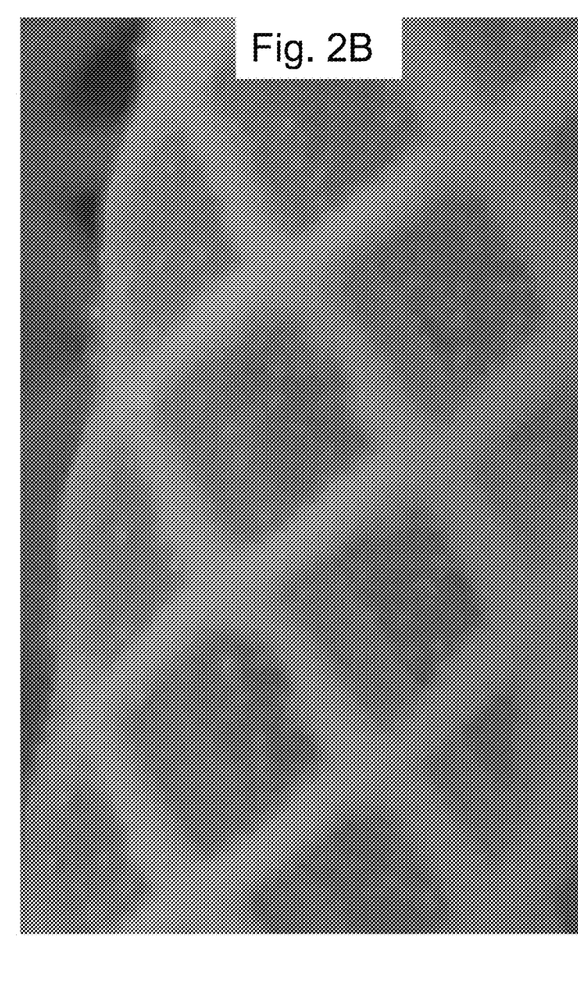

Turning next to FIG. 2, another aspect of the invention is shown which demonstrates that this approach stabilizes PVA against dissolution in aqueous media and permits infiltration with a type I collagen, stem cell and smooth muscle cell matrix.

Figure 3A:
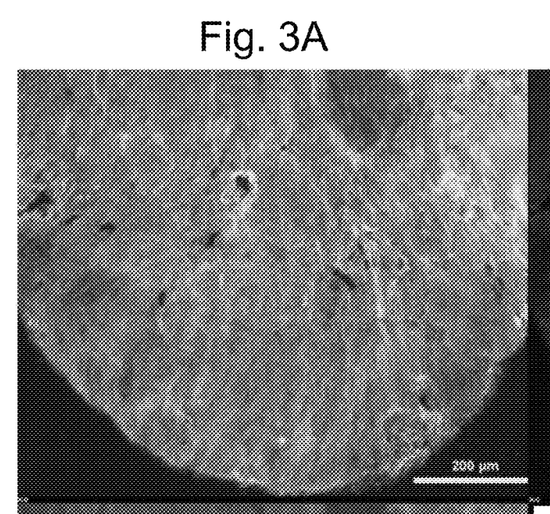
FIGS. 3A, 3B, and 3C are photographs in yellow red and green lights respectively of a cross section of the disclosed type of scaffold showing arrangement of collagen filaments in an 'in-filled' replicate graft.
Figure 3B:
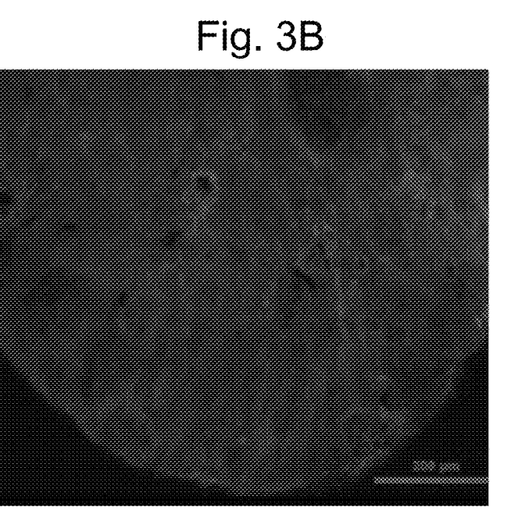
Figure 3C:
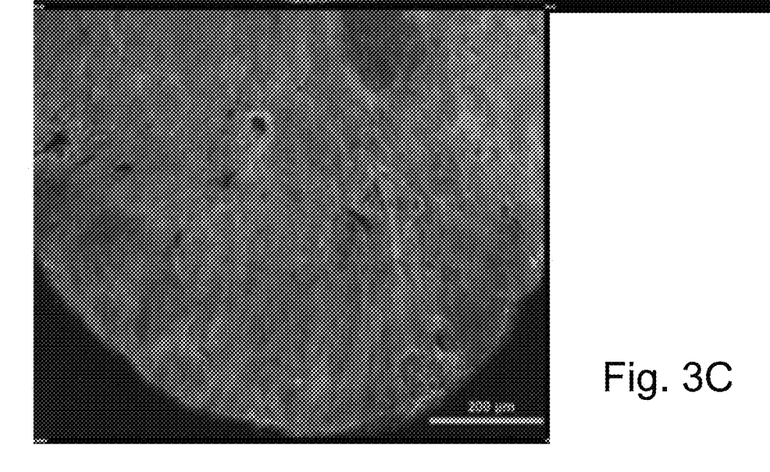

As can be seen in FIG. 3, a second use of the technology is shown is to provide a framework to create an initial 3D frame onto which many different cell types can be integrated to create tissue replacements. These closely resemble normal tissue and provide the opportunity to tailor these devices to patient needs for inexpensive and accessible 'personalized' medicine.

The disclosed use of 3D printing and chemical crosslinking of PVA creates a large number of chemistries to create durable as well as resorbable/flexible scaffolds onto which collagen, cells, and growth factors have been successfully integrated to create blood vessel, heart, skin and bone-like tissue replicants. The disclosed approach was not anticipated based on previous printing. A similar compound was, in fact, described by the manufacturer as a water dissolving matrix intended to lose stability within minutes of exposure to water, thereby effectively teaching against the presently disclosed invention. The properties of the disclosed matrix following modification were determined after development of the chemistries to create stabilized matrices.

The disclosed methods can create highly durable and safe vascular access grafts, coronary artery bypass grafts, skin replacements, duct replacements, bone replacements, and vascular conduits, just for example, which are chemically activated to covalently bind growth factors, guidance molecules and matrix proteins.

3D printing with antimicrobial properties is still in its infancy; with only a limited number studies published that demonstrate the potential of 3D printed antimicrobial materials. Adaptation of new fabrication technologies which incorporate iodine may offer potent and novel anti-infective strategies. Polymer-iodine complexes, known as 'iodophors', are currently in use as antiseptics and in wound care dressings to prevent infection, but have not been examined as a potential 3D antimicrobial agent. Povidone-iodine (PVP-I) is one of the most widely used iodophors and in vitro and in vivo studies have long demonstrated that PVP-I is highly effective against a broad spectrum of bacterial wound isolates and even antibiotic-resistant species. PVP-I is available in many different formulations including solutions, creams, ointments, sprays, and wound dressings and there is evidence that PVP-I may even improve wound healing, for example, significantly increasing the healing rate and reduced healing time in leg ulcers compared to other conventional antiseptics (silver sulfadiazine and chlorhexidine digluconate).

The disclosed research explored another polymer, polyvinyl alcohol (PVA), as a custom 3D print platform for iodization. PVA is a multifunctional polymer, demonstrated by the inventors to be compatible with three-dimensional (3D) printing techniques, such as fused deposition modeling (FDM). Importantly, PVA is a water soluble synthetic polymer, similar to PVP, which is capable of forming a molecular inclusion complex with iodine. PVA-I is effective in iodized foams in wound care management and has a unique color change property which allowing for visual detection of iodine depletion. Iodized PVA materials are initially black/brown and as the iodine is depleted the scaffold returns to its natural color, which ranges from clear to a cream-yellow.

Iodine is also widely applied as an intravascular contrast agent used for computed tomographic (CT), angiographic, and fluoroscopic imaging due to its intrinsic ability to attenuate x-radiation. Incorporation of iodine may be used in construction of various polymers with the purpose of increasing or facilitating radiodensity. Yet, iodine-containing temporary or permanent medical implants are not yet extensively used in clinical practice, reflecting concerns about local and systemic toxicity as well as contrast-induced nephropathy.

Although these iodophors are effective antimicrobial agents, some clinicians have expressed reluctance over iodine's cytotoxicity, which depends on iodophor concentration—and the rate and mechanism of iodine release. Advanced technologies, such as 3D printing, can overcome many of these issues through localizing iodine delivery, allowing for more customized wound care scaffolds to be fabricated to patient-specific anatomies, and adjusting iodine-dosing concentrations that depend on the nature of the wound, including its type and size. In this study, the inventors successfully 3D printed PVA devices, crosslinked the PVA, and then iodized the prints through gaseous sublimation. The disclosed approach provides a highly accessible, inexpensive and 'tunable' architecturally diverse synthetic platform for producing antimicrobial and radiopaque devices and meshes, and opens the door for other embodiments as well.

Figure 4A:
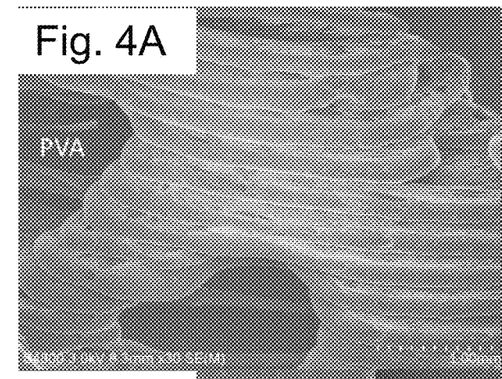
FIGS. 4A-4F are scanning electron microscopic images of 4A) PVA, 4B) PVA-X, 4C) PVA-I, 4D) PVA-X-I, and x-ray images of 4E) PVA-X and 4F) PVA-X-I.
Figure 4B:
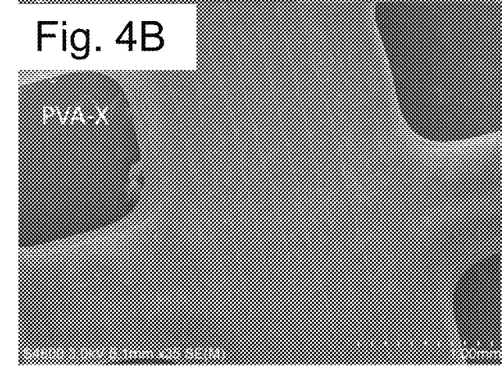
Figure 4C:
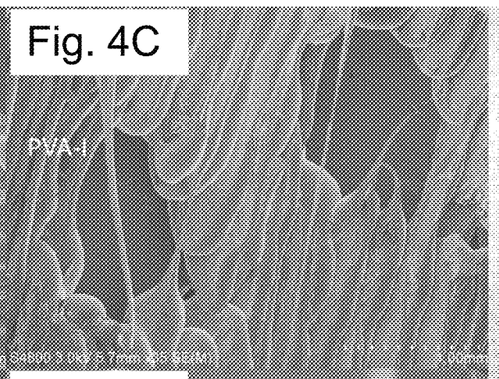
Figure 4D:
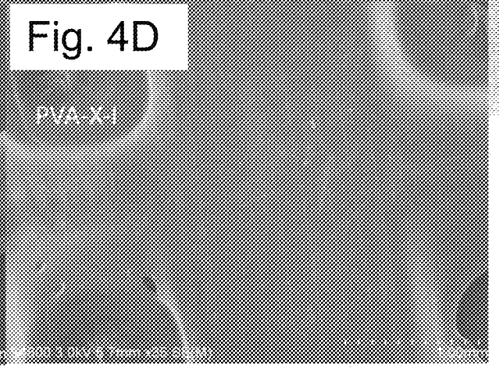
Figures 4E, 4F:
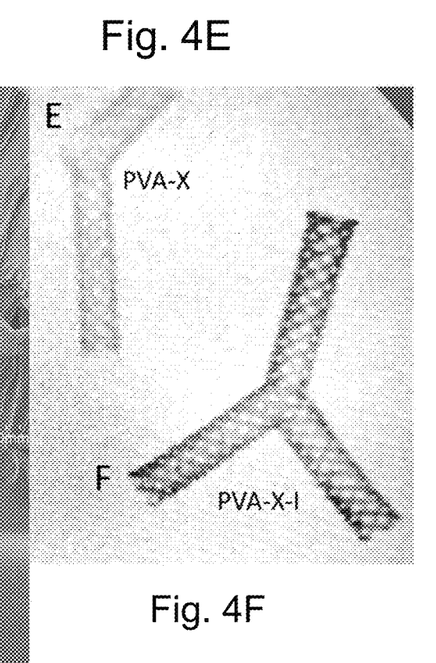
Figure 5A:
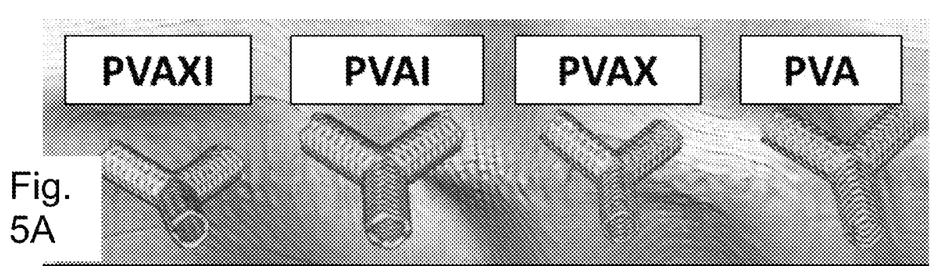
FIGS. 5A-5D are CT image acquisitions of iodine-impregnated and control 3D printed vascular Y-stent substrates. Transaxial (A) CT images of the 3D printed substrate with coronal (B) and 3D coronal reconstructions (C). Illustration of acquiring the Hounsfield units data using an elliptical region of interest on the PVA-I stent (D)
Figure 5B:
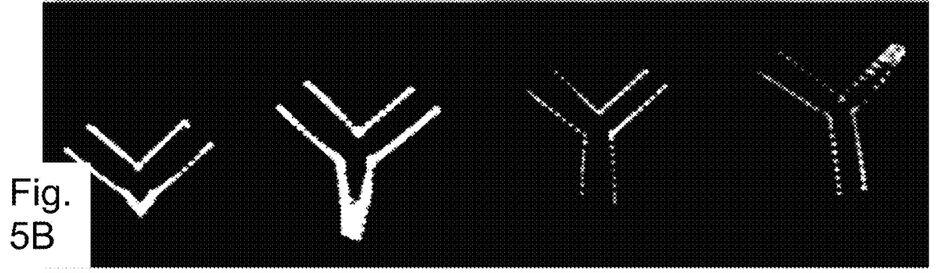
Figure 5C:
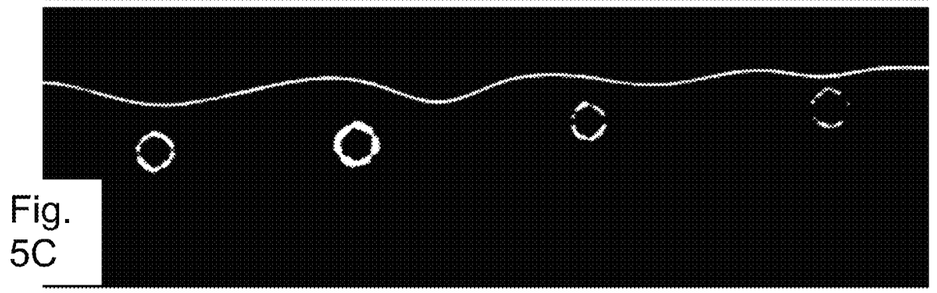
Figure 5D:
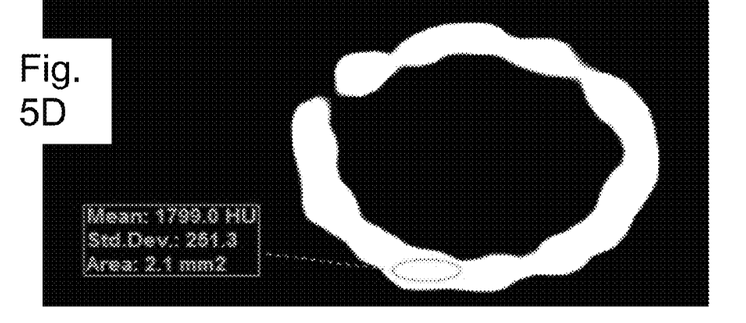
Figure 6A:
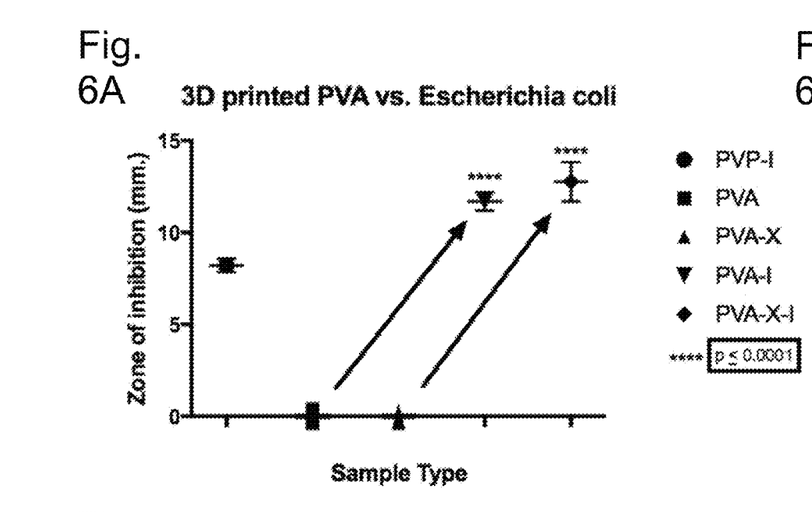
FIGS. 6A-6D are charts displaying the zones of inhibition for substrates against (A) *E. coli* and (B) *S. aureus* in blood agar disc diffusion assays, and images showing 3D printed PVA-X-I samples in blood agar disc diffusion assays against (C) *E. coli* and (D) *S. aureus*.
Figure 6B:
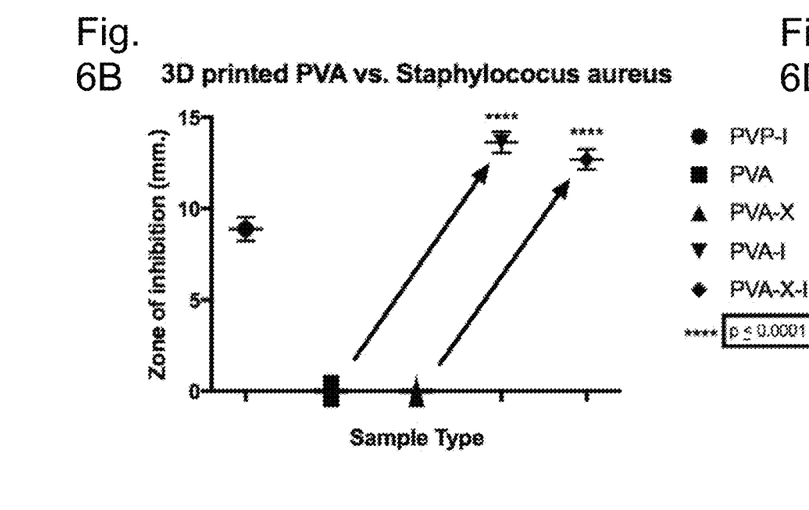
Figure 6C:
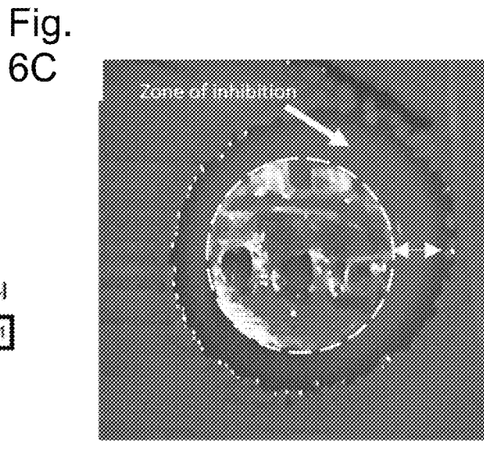
Figure 6D:
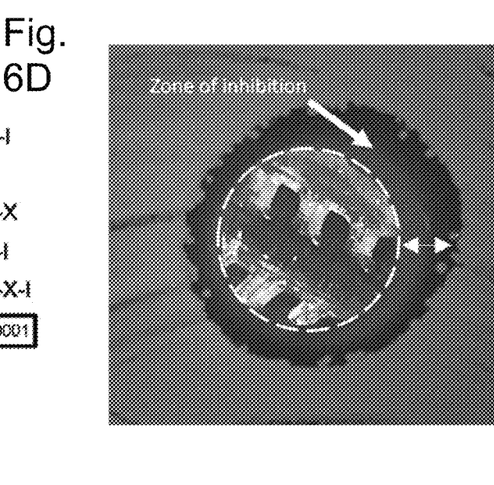

Results:

2.1 Crosslinking Effect on 3D Printed PVA Surfaces:

The utility of iodine gas sublimation as a 3D printed PVA surface modification with antibacterial properties was confirmed in a series of experiments designed to characterize its material properties, interface, and antibacterial inhibitory responses to Gram-negative and Gram-positive bacteria. SEM micrographs showed a smoother and more compact filament topography in cross-linked PVA polymer networks as compared to the non-cross-linked PVA (FIGS. 4A-4D). The iodized PVA prints were also shown to be radiopaque when viewed under x-ray imaging (FIGS. 4E and 4F).

2.2 Imaging Capability of 3D PVA Stents:

For imaging studies, vascular Y-stents made of PVA-I and PVA-X-I were evaluated and found to be dense and readily visible by CT. By comparison PVA and PVA-X were significantly less dense and required windowing to achieve visibility on CT (FIGS. 5A-5D). Quantitatively, PVA-I and PVA-X-I were found to have significantly higher HU values compared to PVA and PVA-X (1666.3 and 1120.7 HU vs 10.7 and 63.0 HU; $p<0.0001$ in both comparisons). PVA-I mean HU of 1666.3 was significantly higher than PVA-X-I (mean 1120.7 HU; $p<0.0001$). There was no significant difference in HU with PVA compared to PVA-X ($p=0.10$).

2.3 Effect of 3D PVA Type on Bacteria Growth:

For antibacterial testing, PVA-I and PVA-X-I were found to release sufficient iodine to inhibit both Gram-negative and Gram-positive bacterial growth during agar disc diffusion assays (FIGS. 6A-6D). For all experiments, the PVA and PVA-I fully dissolved while the PVA-X and PVA-X-I versions maintained hydrogel crosslinked formations. PVA-I meshes inhibited bacterial growths with a mean±standard deviation zone of inhibition of 11.70±0.50 mm (n=3) for *E. coli* and 13.63±0.58 mm (n=3) for *S. aureus*. PVA-X-I meshes inhibited bacterial growths with a mean±standard deviation zone of inhibition of 12.76±1.06 mm (n=3) for *E. coli* and 12.70±0.60 mm (n=3) for *S. aureus*. PVA and PVA-X displayed no zones of inhibition. The PVP-I inhibited bacterial growths with a mean±standard deviation zone of inhibition of 8.20±0.04 mm (n=6) for *E. coli* and 8.88±0.65 mm (n=6) for *S. aureus*. When compared to PVP-I filter paper discs, all samples were significant ($p<0.0001$). For PVA-I vs. PVA-X-I, no significant differences were found for the zones of inhibition (*E. coli* p=0.1923, *S. aureus* p=0.1141). For the PVA vs. PVA-I zones of inhibition, there were significant differences for both *E. coli* and *S. aureus* ($P<0.0001$). For the PVA-X vs. PVA-X-I, significant differences were also noted for both *E. coli* and *S. aureus* ($P<0.0001$).

Discussion:

3D printing techniques have enormous utility in many industrial applications and may be viewed as important tools in future clinical technology development. Medical applications for 3D printing soon may replace many conventional biomaterial-manufacturing approaches, as customizable and on-demand wound care products with localized drug delivery have many diverse applications. A wide range of materials may be explored for medical applications in 3D printing, including, plastics, metals, ceramics, and biological materials. The inventors anticipate that rapid-prototyping and a rapidly expanding catalogue of compatible materials expands the potential for new tissue and organ fabrication techniques in transplantation, as well as new pharmaceuticals and drug delivery systems.

The inventors found that iodine containing 3D printed scaffolds have significantly higher HU values and demonstrated superior visibility on CT. Although the iodine-containing scaffolds without crosslinking (PVA-I) had significantly higher HU (compared to the crosslinked iodine-containing scaffolds (PVA-X-I), this is not likely to be highly meaningful clinically as both were very well-visible (i.e., highly radio-dense) on CT. In this study, the inventors choose an atypical configuration of a vascular stent ('Y-stent') as a proof on principle and to add dimensions/complexity to our 3D printed constructs. In this format, the principle of iodine containing customizable devices demonstrates the value of iodination in custom-constructed 3D printed implants. Therefore, in addition to radiopacity, the iodination of implants, e.g. vascular stents, create materials which have the ability to reduce or poentially eliminate colonization with bacteria (i.e. 'nidus' of infection) and reduce the risk of cellulitis associated with implantation of foreign materials.

3D printing offers the ability to fabricate custom implants with tailored concentrations of iodinated material for imaging and antimicrobial applications. The nature of additive manufacture is such that an iodine-containing layer can be created within the scaffold for extended release or long-term imaging. Through additional polymer coatings, which can be permanent or slow degrading, the iodine prints can be shielded from the outside (reducing toxicity). Additionally, the use of iodine sublimation with printed PVA matrixes allows derivatization in solid phase and avoids the need for aqueous $I_2$/KI mixtures which might dissolve or warp these matrices. Although nephrotoxicity associated with iodinated intravascular contrast media is well-described, recent data suggests its warnings may have somewhat overestimated risk compared to prior estimates. Imaging of iodine diffusion into adjacent tissues might be used to measure iodine abundance, also may be advantageous in non-vascular antimicrobial applications (e.g., iodine-impregnated devices in a non-vascular postoperative cavity).

Conclusions:

To the inventors' knowledge, this is the first report showing that post-3D printed materials can be loaded with iodine through sublimation to exhibit microbiostatic and radiopaque properties. The sublimation process produced molecular iodine gas, which reacted with the PVA hydroxyl groups to form PVA iodine complexes. It is apparent that GA crosslinking appears to reduce at least some of potential binding sites where iodine interacts with PVA, however, crosslinking may generate a PVA hydrogel scaffold with much greater hydrophilic lifetime enabling extended release. Using the disclosed methods, the inventors anticipate that a large variety of wound care products, preferably including bandages, spray coverings, wound plugs, burn garments, meshes, gauzes, hemostatic devices, customized constructs and temporary skin coverings, may be fabricated which can be modified for localized delivery of different rates of iodine release with different intensities of antimicrobial activity by accomplishing different levels of iodine loading and cross linking rates using matrices which have been hydrated to different extents (fully saturated with water vapor=maximal binding vs. fully dried/hygroscopic matrix which has minimal binding) which are treated with sublimed iodine. The realization of scalable and cost-effective antimicrobial biomaterial fabrication techniques may provide clinicians with a new and powerful arsenal of antimicrobial materials. These methods may also be potentially used with larger custom sublimation chambers which used higher pressure and temperature conditions to achieve more uniform loading to synthesize iodized 3D printed PVA objects at an industrial-scale amounts or produce relatively smaller in-house productions at health-care facilities. These methods may also be potentially used with larger custom sublimation chambers. On example is industrial scale 3D printers print PVA meshes. The meshes go down conveyor belts to a cross-linking and iodizing chamber. The material is then run through saws that cut the larger meshes to smaller meshes for packaging. Overall, the iodized 3D prints created through sublimation provides a foundation for future researchers to explore and has potential uses as medical devices, wound dressings, and antimicrobial surfaces, just for example.

Experimental Section:

Synthesis of Iodized PVA Scaffolds:

PVA filaments (AquaSolve™, Formfutura, Nijmegen, The Netherlands, 1.75 mm diameter) were 3D printed into mesh patterns at 201° C. using a consumer grade MakerBot replicator desktop 3D printer (MakerBot Industries LLC, Brooklyn, N.Y.). For control and experimental samples, circular discs (0.60 mm diameter and 0.2 mm thickness) were cut from the 3D printed meshes using a sterile hole punch prior to iodine loading, electron microscopy, and agar-disc diffusion antibacterial assays. Additional PVA samples were immersed in distilled water, dried at 25° C. (1 h), and cross-linked by placing the PVA models in a gas-vapor desiccator containing two separate 50 ml containers containing: 1) 20 mL of 4% glutaraldehyde ('GA') (EMD Millipore Corporation, Darmstadt, Germany) and 2) 10 mL of concentrated hydrochloric acid (HCL) (Fisher Scientific, Hampton, N.H.) at 42° C. for 24 hours. Cross-linked PVA scaffolds were then rinsed extensively in distilled water, and air dried for 24 hours. For iodine loading, PVA and crosslinked PVA (PVA-X) meshes were placed in a closed chamber containing 110 mg of iodine crystals (Mallinckrodt Pharmaceuticals, St. Louis, Mo.). The samples were incubated at 42° C. for 24 hours to produce gaseous iodine through sublimation which generated PVA loaded with iodine (PVA-I) and PVA-X loaded with iodine (PVA-X-I). Iodized samples were next removed from the chamber and air dried for 24 hours. Vascular Y-stents were also printed with PVA and subjected to the same crosslinking and iodine loading procedures for CT imaging.

Scanning Electron Microscopy and X-Radiation Imaging:

3D printed surface topographies were characterized with a S-4800 field-emission scanning electron microscope (SEM) (HITACHI, Tokyo, Japan). Samples were mounted on double-sided adhesive carbon tape and attached to the working stage. X-ray imaging was accomplished using an OEC 9900 Elite C-Arm System by General Electric (Fairfield, Conn.).

Image Acquisition with Computed Tomography:

Trans-axial CT images of the iodine-impregnated scaffolds of simulated Y-vascular stents were acquired using a Siemens Biograph PET/CT scanner (Siemens, Munich, Germany) with a kVp of 120 and slice thickness of 0.6 mm. Coronal and sagittal reconstructions were constructed at the image acquisition workstation. Images were analyzed using Osirx (Pixmeo SARL, Bernex, Switzerland) and Vitrea Enterprise Suite (Vital Images, Inc., Minnetonka, Minn., USA). Hounsfield units (HU) of each scaffold were measured using a small elliptical region of interest. Three HU were acquired for each of the four scaffolds. Mean HU for each scaffold were compared with one another using Student's t-test.

Evaluation of Antimicrobial Potential of Iodized PVA Scaffolds:

*Escherichia coli* (*E. coli*) and *Staphylococcus aureus* (*S. aureus*) were used to create 0.5 McFarland standard bacterial suspensions and 50 microliters (μL) of suspension were added to human blood agar plates for incubation with samples. Each series was tested in triplicate and incubated for 24 hr at 37° C. Paper discs were loaded with 10 μl of Triadine povidone-iodine solution (PVP-I) (Triad Group Inc., Brookfield, Wis.) and also tested with 3D printed samples. For all disc diffusion assays, the bacterial zones of inhibition (ZOI) were measured with a digital caliper. Mean zones of inhibition for each sample type were compared with one another using Student's t-test for both *E. coli* and *S. aureus*.

Further Embodiments:

Polymer Source Material:

While PVA is preferable as the structural source material, other alcholol containing polyers could also be used.

Crosslink Material (Crosslinkers):

While glutaraldehyde (pentanedial) is preferable to establish the cross links in the PVA, potentially any polyaldehyde would work, including ethanedial, propanedial, butanedial, hexanedial, heptanedial, octanedial, nonanedial, decandial. This broad class of structures could be used in the crosslinking process for a variety of tailored applications; such as controlled degradation rates and drug releases based on angstrom level crosslinking and additional functional groups or structures. The inventors have also made crosslinked PVA with 1,10 didecanal and therefore believe that other dialdehydes would also work as well, including any long-chain dialdehydes, o-Phthalaldehyde, or branched polyaldehydes, to produce crosslinked PVA with slightly different flexibility and solubility properties. Different cross-linking may also be used for specific protein binding and functionalization, for example. The amount of crosslinkers may be increased or decreased, by a factor of 10 each way, for example. A higher amount or concentration of crosslinkers would yield a harder and more brittle product, whereas a smaller amount or lower concentration of crosslinkers would yield a softer product.

Cross Link Process:

Though the disclosed method(s) above are prefered, other methods may be used to establish the cross links in the PVA. Crosslinking faciliators include exposuer to acid (HCL, acetic acid vapor, e.g.), trimesoyl chloride (TMC)/hexane with carboxylic acid anhydride (reaction with PVA leads to vinyl alcohol-vinyl ester copolymers), PVA/sulfoacetic acid can from crosslinked hydrogel, (PVA) can be esterified and crosslinked with chemicals such as 10-undecenoyl chloride, high energy or ion beam (gamma beam and/or electron beam radiation [including at room temperature], for example), In the disclosed embodiment, the PVA was exposed to a heat at a level of 42° C. and HCL acid vapor. In altrnative embodiments, acid may be omited and/or the level of heat may be changed for the process of cross-linking the PVA with GA. The melting point of polyvinyl alcohol is 200° C. Any temperature over this will likely damage the 3D shape, so temperatures at and above 200° C. are preferably avoided. It is anticipated that a preferred working range for the crosslinking process when elevated heat is used is between around 40° C. and 130° C. The time for the crosslinking process is preferably between 6 and 48 hours. The longer the exposure to crosslinking facilitators (e.g., heat, acid, gamma ray, etc.) the equals higher cross linking of the PVA. The shorter the time exposed to crosslinking facilitators, the less cross linking of the PVA. For larger/thicker structures, preferably a longer crosslinking time is provided, whereas for smaller/thinner structures, less time may be required. For a faster rate of crosslinking, exposure to multiple crosslinking facilitators is preferable (both acid and elevated temperature, for example), or a greater intensity of a single crosslinking facilitator (higher temperatures or higher concentration of acid, for example).

Medically Functional Chemical Addition:

"Medically functional chemicals" include chemicals with antimicrobial properties, with anti-cancer properties, that are therapeutic for other diseases or conditions (e.g., cardiovascular disese, isceamea, Parkensen's disease), and/or that are radiopaque. Iodine is an advantageous medically functional chemical due to the natural gas sublimation that occurs even at room temperature. Typically, transition metals can display radiopaque and antibacterial properties. However, they do not spontaneously sublimate into molecular gases like iodine. Further, the small size of molecular iodine is easily infiltrated into many different porous polymer matrixes. Additional medically functional chemical additions include regulatory, matrix and guidance molecules without which grafts often fail, growth factors, peptides, and/or cells, type I collagen, stem cell and smooth muscle cell matrix. Additional medically functional chemical additions include therapeutics, such as pharmaceuticals, and drugs, and substances that are beneficial for the prevention and/or cure of diseases and conditions and/or promotion of healing, not limited to cancer and bacterial infection.

For protein amine medically functional chemicals, according to one embodiment, the aldehyde crosslinked PVA print is simply immersed in the protein amine containing solution, and allow to bind overnight at room temperature, for example. This could be performed with non-covalent ionic binding as well for other materials. There are a variety of chemistries that can be applied to crosslinked PVA.

Though gas sublimation is perfered for iodine, the iodine may be bound to the PVA by means other than gas sublimation. The PVA print may be simply immersed in iodine solution, which would accomplish similar binding, but would preferably be followed by additional rinsing and drying steps not required for iodizing via gas sublimation. Typically, iodine solutions such as Povidone-iodine (PVP-I) contain low concentrations of iodine and are already in iodophor forms (polymer bounded). Gas sublimation is an ideal loading method with controllable dosages and full penetration The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

We claim:

1. A method for creating a medical device comprising:
   3D printing the medical device out of polyvinyl alcohol; and
   crosslinking the polyvinyl alcohol with an aldehyde;
   wherein the medical device is a vascular stent; and
   the aldehyde has three or more Carbon atoms.

2. The method of claim 1 wherein the crosslinking of the polyvinyl alcohol with the aldehyde is facilitated with an acid.

3. The method of claim 2 wherein the acid is HCl.

4. The method of claim 1 wherein the crosslinking of the polyvinyl alcohol with the aldehyde is facilitated by elevating a temperature of the polyvinyl alcohol and the aldehyde to a temperature of between 40 degrees and 200 degrees for a set time.

5. The method of claim 4 wherein the set time is between 6 and 48 hours.

6. The method of claim 1 wherein the crosslinking of the polyvinyl alcohol with the aldehyde is facilitated by exposure to one of gamma and electron beam radiation.

7. The method of claim 1 further comprising the step of loading a medically functional chemical onto the polyvinyl alcohol.

8. The method of claim 7 wherein the medically functional chemical is one of iodine, one of Bromine, a divalent cation, a protein, an antibiotic, an anti-cancer drug, a therapeutic, a regulatory molecule, a matrix molecule, a guidance molecule, a growth factor, collagen, a stem cell matrix, a smooth muscle cell matrix, and a cell.

9. The method of claim 7 wherein the medically functional chemical is iodine and further comprising a step of loading the iodine on the polyvinyl alcohol via gas sublimation.

10. The method of claim 1 wherein the aldehyde is one of propanedial, butanedial, hexanedial, heptanedial, octanedial, nonanedial, decandial.

11. The method of claim 1 wherein the aldehyde is 1,10 didecanal.

12. The method of claim 1 wherein the aldehyde is one of a long-chain dialdehyde, o-Phthalaldehyde, and a branched polyaldehyde, wherein the long chain dialdehydes have at least 10 Carbon atoms.

13. The method of claim 1 further comprising using patient anatomy to generate custom replicants based on MR or CT imaging.

14. A method for creating a medical device comprising:
    3D printing the medical device out of polyvinyl alcohol, and exposing the PVA to a heat at a level of 42° C. and HCL acid vapor.

15. The method of claim 14 further comprising crosslinking for at least 6 hours.

16. The method of claim 14 further comprising the step of forming the medical device into one of a vascular stent, a product for use in a non-vascular anatomical space, a wound care product, a wound dressing, an antimicrobial surface, a vascular access graft, a coronary artery bypass grafts, a skin replacement, a duct replacement, a bone replacement, and a vascular conduit.

* * * * *